(12) United States Patent
Ju et al.

(10) Patent No.: US 11,311,319 B2
(45) Date of Patent: Apr. 26, 2022

(54) UNILATERAL NAIL HOLDER

(71) Applicant: HEBEI RUIHE MEDICAL DEVICES CO., LTD., Shijiazhuang (CN)

(72) Inventors: Chonghe Ju, Shijiazhuang (CN); Yan Li, Shijiazhuang (CN); Cang Shao, Shijiazhuang (CN)

(73) Assignee: HEBEI RUIHE MEDICAL DEVICES CO., LTD., Shijiazhuang (CN)

( * ) Notice: Subject to any disclaimer, the term of this patent is extended or adjusted under 35 U.S.C. 154(b) by 0 days.

(21) Appl. No.: 17/244,750

(22) Filed: Apr. 29, 2021

(65) Prior Publication Data
US 2021/0244450 A1 Aug. 12, 2021

Related U.S. Application Data

(63) Continuation of application No. PCT/CN2019/105919, filed on Sep. 16, 2019.

(30) Foreign Application Priority Data

Nov. 2, 2018 (CN) .......................... 201811300353.8

(51) Int. Cl.
*A61B 17/70* (2006.01)
(52) U.S. Cl.
CPC ................................ *A61B 17/7076* (2013.01)
(58) Field of Classification Search
CPC .................. A61B 17/70; A61B 17/7074–7091
See application file for complete search history.

(56) References Cited

U.S. PATENT DOCUMENTS

| 2004/0249378 | A1* | 12/2004 | Saint Martin | A61B 17/7032 606/86 A |
| 2008/0125788 | A1* | 5/2008 | Cohen | A61B 17/708 606/104 |
| 2011/0288592 | A1 | 11/2011 | McKinley | |
| 2012/0290011 | A1* | 11/2012 | Justis | A61B 17/7076 606/278 |
| 2016/0302838 | A1* | 10/2016 | Cormier | A61B 17/7074 |

(Continued)

FOREIGN PATENT DOCUMENTS

| CN | 202637097 U | 1/2013 |
| CN | 202776530 U | 3/2013 |

(Continued)

*Primary Examiner* — Eduardo C Robert
*Assistant Examiner* — Michelle C Eckman
(74) *Attorney, Agent, or Firm* — Slater Matsil, LLP

(57) ABSTRACT

The application provides a unilateral nail holder, including: a holding rod having a lower end provided with a clamping groove for receiving a single side plate of a pedicle screw; a fixing hook connected to the holding rod, where the fixing hook is located at an inner rear side of the clamping groove, a rear side of the single side plate is provided with a fixing hole, and the fixing hook hookable with the fixing hole; and a separating mechanism provided between the holding rod and the fixing hook for pushing the fixing hook to withdraw from the fixing hole. The fixing hook is hooked with the fixing hole on the rear side of the single side plate, the single side plate is limited in the clamping groove, and the clamping of the pedicle screw is realized.

8 Claims, 8 Drawing Sheets

(56) References Cited

U.S. PATENT DOCUMENTS

| | | | |
|---|---|---|---|
| 2018/0014863 A1* | 1/2018 | Biester | A61B 17/8615 |
| 2019/0183541 A1* | 6/2019 | Lee | A61B 17/7082 |
| 2019/0274741 A1* | 9/2019 | Vazifehdan | A61B 17/7086 |

FOREIGN PATENT DOCUMENTS

| | | |
|---|---|---|
| CN | 104688326 A | 6/2015 |
| CN | 204446088 U | 7/2015 |
| CN | 206924110 U | 1/2018 |
| CN | 109077790 A | 12/2018 |
| CN | 109077792 A | 12/2018 |
| CN | 209332233 U | 9/2019 |

\* cited by examiner

UNILATERAL NAIL HOLDER

CROSS-REFERENCE TO RELATED APPLICATIONS

This application is a continuation application of International Application No. PCT/CN2019/105919, filed on Sep. 16, 2019, which claims priority to Chinese Patent Application No. CN 201811300353.8, filed on Nov. 2, 2018. The disclosures of the aforementioned applications are hereby incorporated herein by reference in their entireties.

TECHNICAL FIELD

The application belongs to the technical field of medical instruments, and particularly relates to a unilateral nail holder.

BACKGROUND

According to a existing pedicle screw, two side plates are arranged at the top of the main body of the pedicle screw, and the two side plates are used for being connected to a fixing screw. In use, the outer sides of the two side plates of the pedicle screw can be clamped by a clamping tool similar to a clamp, such that the pedicle screw can be installed. However, a clamping tool with such structure clamps the two side plates of the pedicle screw, such that the top of the pedicle screw can be completely shielded. It is to the disadvantage of the position alignment of the pedicle screw, the installation and fixation of a screw in an installation groove of the pedicle screw, and like operations.

SUMMARY

These and other problems are generally solved or circumvented, and technical advantages are generally achieved, by embodiments of the present disclosure which provide a unilateral nail holder.

Technical Problems

The application provides a unilateral nail holder, and aims to solve the technical problem in the prior art that when a clamping tool is used, the top of a pedicle screw is completely shielded, which affects the subsequent operation.

Technical Solutions

The technical scheme adopted by the application is to provide a unilateral nail holder, which comprises: a holding rod, where the lower end of the holding rod is provided with a clamping groove for receiving a single side plate of a pedicle screw; a fixing hook connected to the holding rod, where the fixing hook is located at an inner rear side of the clamping groove, a rear side of the single side plate is provided with a fixing hole, and the fixing hook is used for hooking with the fixing hole; and a separating mechanism provided between the holding rod and the fixing hook for pushing the fixing hook out of the fixing hole.

In one embodiment, the separating mechanism comprises: a pushing core slidably connected to the holding rod, axially sliding along the holding rod; a separating protrusion provided on the fixing hook; and a separating ramp provided at a lower end of the pushing core, where the separating ramp is in sliding fit with the separating protrusion, and is used for pushing the separating protrusion backward.

In one embodiment, a front side of the holding rod is provided with a sliding groove arranged along a long axis of the holding rod, and an inner wall of the sliding groove is provided with a limiting protrusion; the pushing core is provided in the sliding groove in a sliding mode, and a side surface of the pushing core is provided with an abutting protrusion which is located above the limiting protrusion and is used for abutting against the limiting protrusion.

In one embodiment, a lower end of the sliding groove is communicated with an upper end of the clamping groove, and the lower end of the pushing core is used for being inserted into the clamping groove.

In one embodiment, a front side surface of the lower end of the pushing core is recessed to form an operation space for communicating with an installation groove of the pedicle screw.

In one embodiment, a rear side of the lower end of the pushing core is provided with a separating groove, an inner wall surface of the separating groove is an arc-shaped curved surface of which an upper end and a lower end are respectively warped backward, and the lower end forms the separating ramp.

In one embodiment, the separating protrusion is received in the separating groove, and the front wall surface of the separating protrusion is an arc-shaped curved surface of which an upper end and a lower end are respectively warped backward.

In one embodiment, the holding rod includes: a handle provided with a sliding hole for receiving an upper end of the pushing core; and an extension rod connected to a lower end of the handle, wherein the clamping groove is provided on a lower end surface of the extension rod, and the fixing hook is elastically connected to the extension rod.

In one embodiment, the front side surface of the lower end of the pushing core is recessed to form an operation space for communicating with the installation groove of the pedicle screw, and the upper end of the pushing core is provided with a through hole communicated with the operation space and for being opposite to the installation groove.

In one embodiment, a lower end of the extension rod is provided with a receiving groove communicating with the rear side of the clamping groove; the fixing hook is provided in the receiving groove, and a hook portion of the fixing hook penetrates into the clamping groove from the receiving groove.

In one embodiment, a lower side surface of the hook portion of the fixing hook is a ramp with a front end inclined upward.

In one embodiment, a front side of the clamping groove is opened, and a width of a front side opening of the clamping groove is smaller than the width of a rear side of the clamping groove.

In one embodiment, the clamping groove is fan-shaped in cross section.

Advantageous Effects of the Disclosure

When the unilateral nail holder according to the application is used, the single side plate of the pedicle screw is inserted into the clamping groove, and then with the fixing hook being hooked with the fixing hole at the rear side of the single side plate, the single side plate is limited in the clamping groove so as to clamp the pedicle screw. After the pedicle screw is put into a predetermined position, the fixing hook is pushed by the separating mechanism such that the fixing hook is pushed out of the fixing hole, and the limiting of the fixing hook to the single side plate is released, making the single side plate slide out of the clamping groove. The unilateral nail holder according to the application can realize the clamping of the pedicle screw by using the single side plate such that the shielding of the top of the pedicle screw is reduced which is convenient for subsequent operation.

The foregoing has outlined rather broadly the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims.

Figure 1:
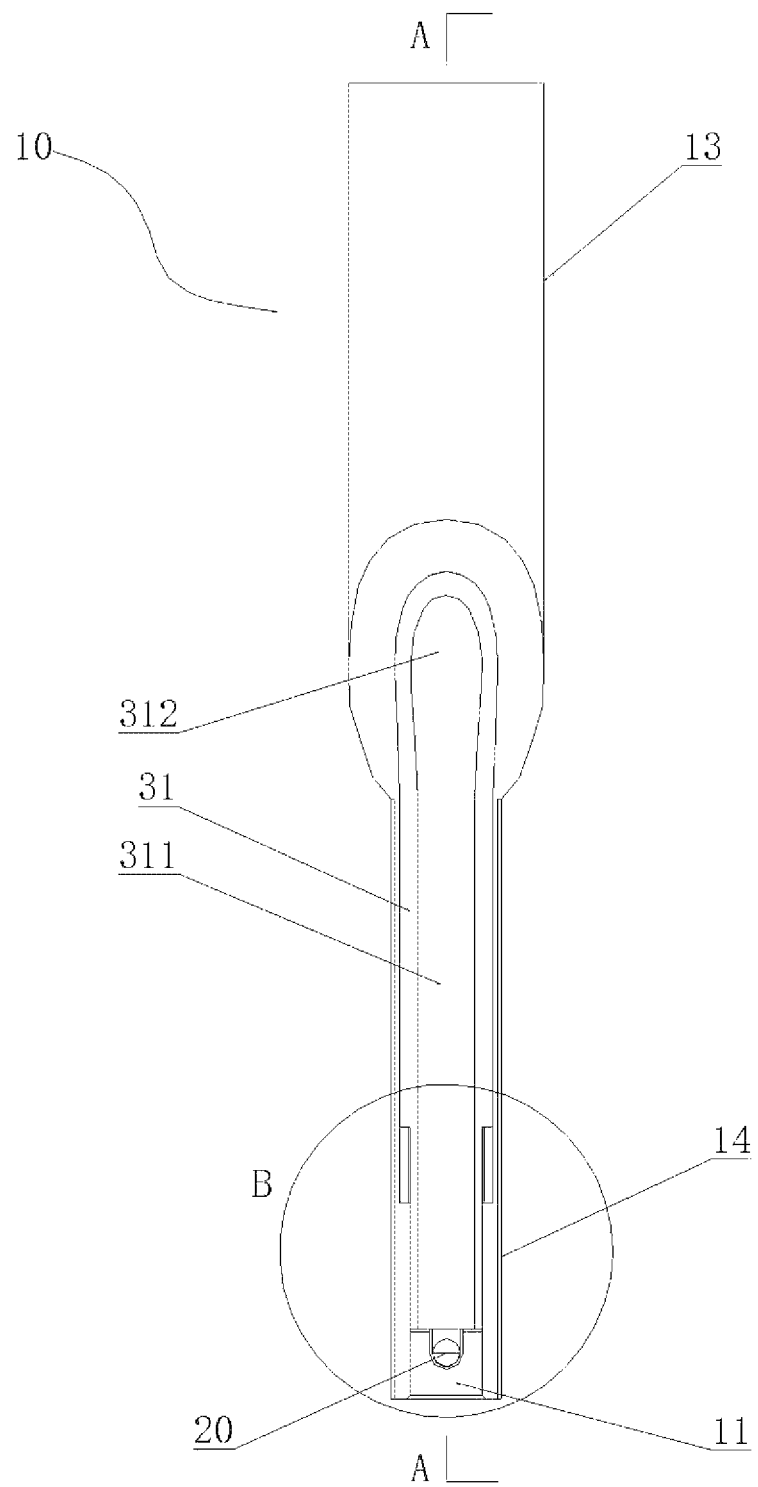
FIG. 1 is a front view of a unilateral nail holder provided according to an embodiment of the application.
Figure 2:
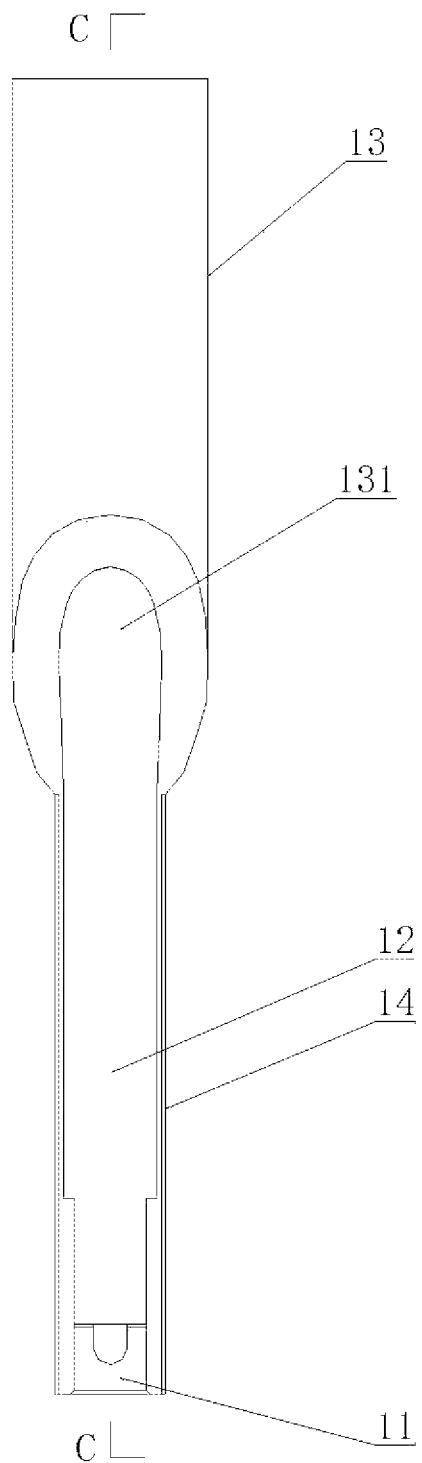
FIG. 2 is a front view of a holding rod of the unilateral nail holder of FIG. 1.

All the reference numerals in the drawings are as follows: 10—holding rod; 11—clamping groove; 12—sliding groove; 121—limiting protrusion; 13—handle; 131—sliding hole; 14—extension rod; 141—receiving groove; 20—fixing hook; 30—separating mechanism; 31—pushing core; 311—operation space; 312—through hole; 313—abutting protrusion; 32—separating protrusion; 34—separating groove; 40—side plate; 41—fixing hole; and 60—installation groove.

Corresponding numerals and symbols in the different figures generally refer to corresponding parts unless otherwise indicated. The figures are drawn to clearly illustrate the relevant aspects of the various embodiments and are not necessarily drawn to scale.

DETAILED DESCRIPTION OF ILLUSTRATIVE EMBODIMENTS

The making and using of the embodiments of this disclosure are discussed in detail below. It should be appreciated, however, that the concepts disclosed herein can be embodied in a wide variety of specific contexts. The specific embodiments discussed are merely illustrative, and do not limit the scope of the claims.

In order to make the technical problems, technical solutions, and beneficial effects to be solved by the application clearer, the following further describes the application in detail with reference to the accompanying drawings and embodiments. It should be understood that the specific embodiments described herein are merely illustrative of the application and are not intended to be limiting thereof.

Referring to FIGS. 1-8 together, a unilateral nail holder provided in an embodiment of the application will now be described. The unilateral nail holder includes a holding rod 10, a fixing hook 20, and a separating mechanism 30.

The lower end of the holding rod 10 is provided with a clamping groove 11 for receiving a single side plate 40 of a pedicle screw. The fixing hook 20 is connected to the holding rod 10, the fixing hook 20 is located at the inner rear side of the clamping groove 11, the rear side of the single side plate 40 is provided with a fixing hole 41, and the fixing hook 20 is used for hooking with the fixing hole 41. A separating mechanism 30 is provided between the holding rod 10 and the fixing hook 20 for pushing the fixing hook 20 out of the fixing hole 41.

Compared with the prior art, when the unilateral nail holder according to the embodiment of the application is used, firstly the single side plate 40 of the pedicle screw is inserted into the clamping groove 11, and then with the fixing hook 20 being hooked with the fixing hole 41 at the rear side of the single side plate 40, the single side plate 40 is limited in the clamping groove 11 so as to clamp the pedicle screw. After the pedicle screw is put into a predetermined position, the fixing hook 20 is pushed by the separating mechanism 30 such that the fixing hook 20 is pushed out of the fixing hole 41, and the limiting of the fixing hook 20 to the single side plate 40 is released, making the single side plate 40 slide out of the clamping groove 11. The unilateral nail holder according to the embodiment of the application can realize the clamping of the pedicle screw by using the single side plate 40 such that the shielding of the top of the pedicle screw is reduced which is convenient for subsequent operation.

In the embodiment, the single side plate 40 of the pedicle screw can be inserted into the clamping groove 11 at the lower end of the holding rod 10, and the rear side of the clamping groove 11 is provided with an opening such that the fixing hook 20 can enter the clamping groove 1 from the rear side to realize the hooking of the fixing hook 20 with the fixing hole 41 at the rear side of the single side plate 40. The separating mechanism 30 can withdraw the fixing hook 20 from the rear side of the clamping groove 11 by pushing the fixing hook 20 backward, thereby withdrawing the fixing hook 20 from the fixing hole 41.

Specifically, the fixing hook 20 is elastically connected to the holding rod 10 such that it is ensured that the fixing hook 20 can be reset under the action of elastic force after the single side plate 40 is inserted into the clamping groove 11.

Referring to FIGS. 1 and 4-8 together, as a specific implementation mode of the unilateral nail holder provided herein, the separating mechanism 30 includes a pushing core 31, a separating protrusion 32, and a separating ramp.

The pushing core 31 is slidably connected to the holding rod 10 and axially slides along the holding rod 10. The separating protrusion 32 is provided on the fixing hook 20. The separating ramp is provided at the lower end of the pushing core 31, is in sliding fit with the separating protrusion 32, and is used for pushing the separating protrusion 32 backward.

In the embodiment, the pushing core 31 slides upwards along the holding rod 10 to drive the separating ramp to move, and then pushes the separating protrusion 32 to move backward, such that the fixing hook 20 connected to the separating protrusion 32 moves backward, and the fixing hook 20 is withdrawn from the rear side of the clamping groove 11, and the fixing hook 20 is withdrawn from the fixing hole 41. The separating ramp may be an inclined plane in which the upper end is inclined forward. The separating protrusion 32 is located above the separating ramp. When the pushing core 31 drives the separating ramp to move upward, the separating ramp pushes the separating protrusion 32 rearward, thereby pushing the fixing hook 20 rearward from the fixing hole 41.

Figure 4:
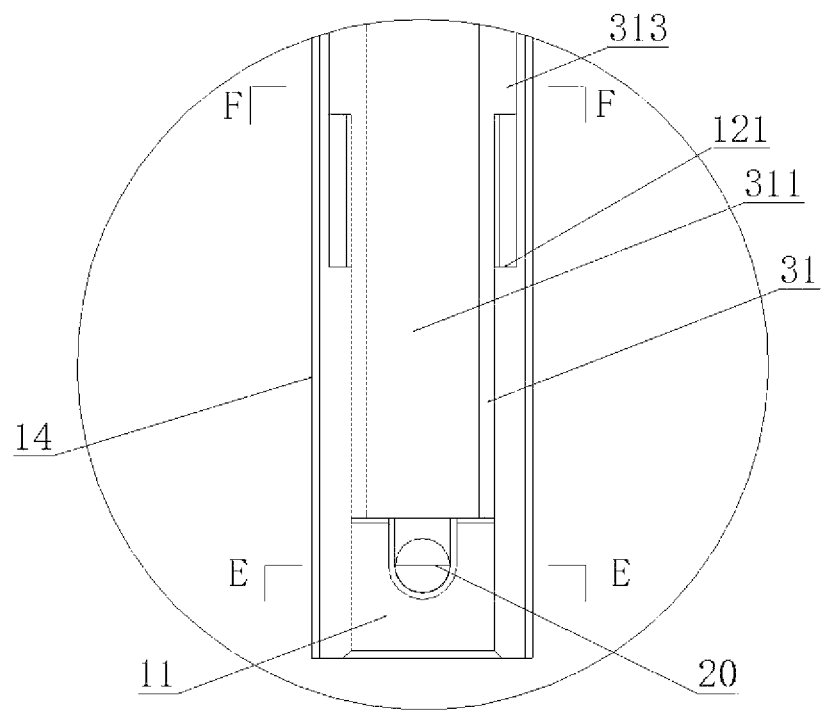
FIG. 4 is an enlarged view at B in FIG. 1.

Referring to FIGS. 1 and 4 together, as a specific implementation mode of the unilateral nail holder provided by the application, the front side of the holding rod 10 is provided with a sliding groove 12 arranged along the long axis of the holding rod 10, and the inner wall of the sliding groove 12 is provided with a limiting protrusion 121; the pushing core 31 is slidably provided in the sliding groove 12, and the side surface of the pushing core 31 is provided with an abutting protrusion 313 located above the limiting protrusion 121 and used for abutting against the limiting protrusion 121. It is avoided that the pushing core 31 protrudes out of the surface of the holding rod 10.

In the embodiment, the side surface of the pushing core 31 is provided with an abutting protrusion 313, and the corresponding sliding groove 12 of the holding rod 10 is provided with a limiting protrusion 121 located below the abutting protrusion 313. When the pushing core 31 moves downwards along the sliding groove 12, the limiting protrusion 121 limit the downward movement distance of the pushing core 31 by limiting the downward movement distance of the abutting protrusion 313, such that the pushing core 31 is prevented from being detached from the sliding groove 12.

Referring to FIGS. 1, 4, 7, and 8 together, as a specific implementation mode of the unilateral nail holder provided in the application, the lower end of the sliding groove 12 communicates with the upper end of the clamping groove 11, and the lower end of the pushing core 31 is adapted to be inserted into the clamping groove 11.

When the pedicle screw is clamped, the single side plate 40 of the pedicle screw is inserted into the clamping groove 11 from bottom to top, then the fixing hook 20 is hooked into the fixing hole 41, the single side plate 40 is limited in the clamping groove 11, and finally, the lower end of the pushing core 31 abuts against the upper end surface of the single side plate 40 by pushing the pushing core 31 downwards, such that the fixing hook 20, the clamping groove 11, and the lower end of the pushing core 31 jointly clamp the single side plate 40. Therefore, the wobbling of the pedicle screw is effectively prevented, the stability of clamping the pedicle screw by the unilateral nail holder is improved, and the subsequent operation of the pedicle screw is facilitated.

Referring to FIGS. 1, 4, 6, and 8 together, as a specific implementation mode of the unilateral nail holder provided in the application, the front side surface of the lower end of the pushing core 31 is recessed to form an operation space 311 for communicating with an installation groove 60 of the pedicle screw.

In the embodiment, between two side plates 40 on the top of the pedicle screw is the installation groove 60 for installing a fixing screw. The front side surface of the lower end of the pushing core 31 is recessed to form an operation space 311, such that the lower end of the pushing core 31 does not shield the installation groove 60, and the installation of the fixing screw is facilitated. More specifically, the front side surface of the pushing core 31 is an arc surface that is arranged along the long axis of the pushing core 31 and has an arc-shaped cross section.

Figure 7:
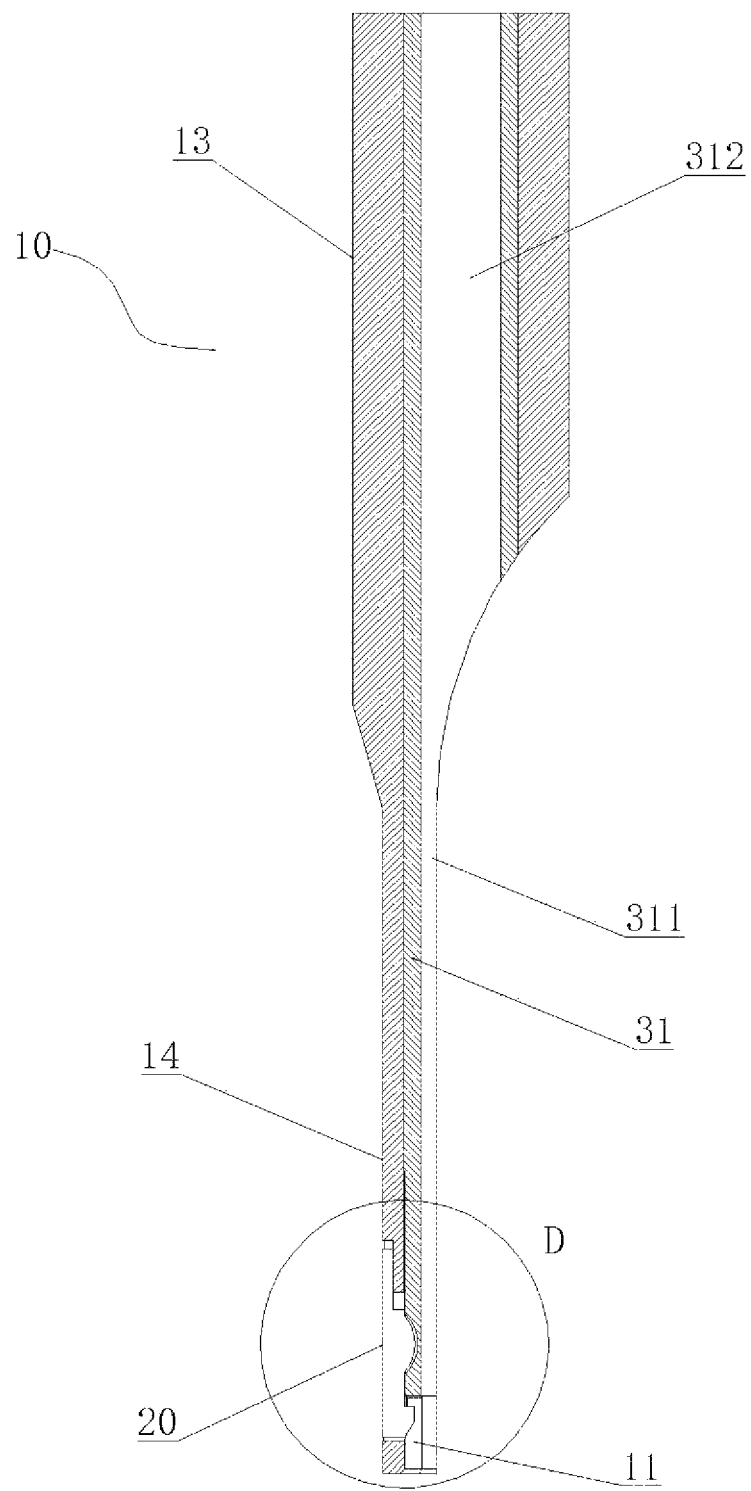
FIG. 7 is a sectional view at A-A in FIG. 1.
Figure 8:
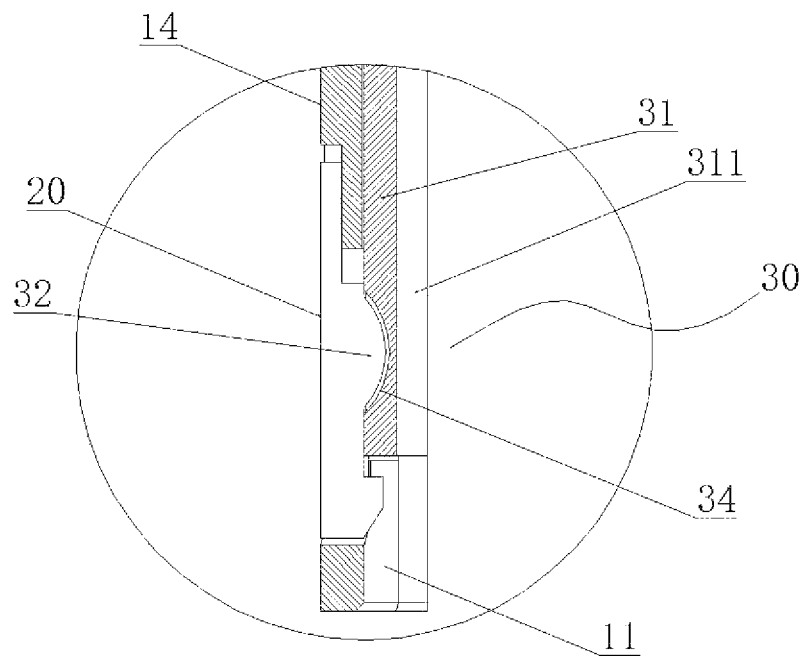
FIG. 8 is an enlarged view at D in FIG. 7.
Figure 9:
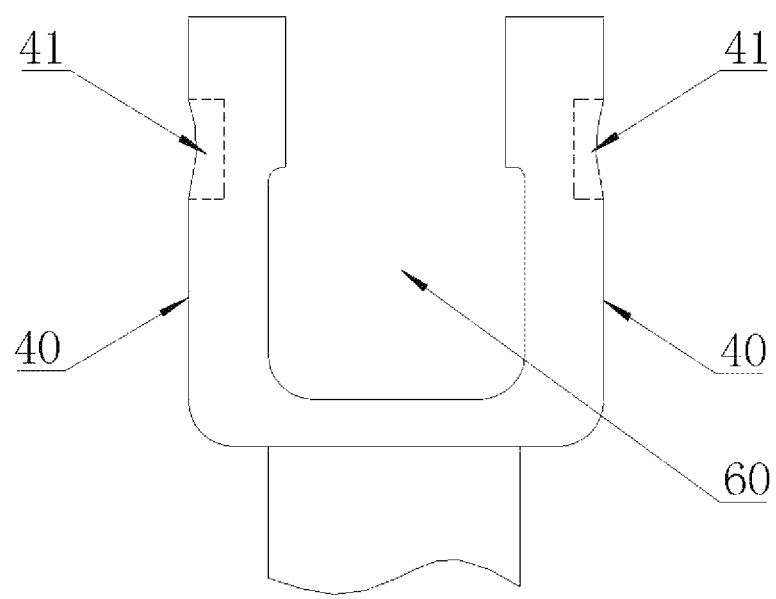
FIG. 9 is a front view of a pedicle screw that can be held by a unilateral nail holder according to an embodiment of the application.
Figure 10:
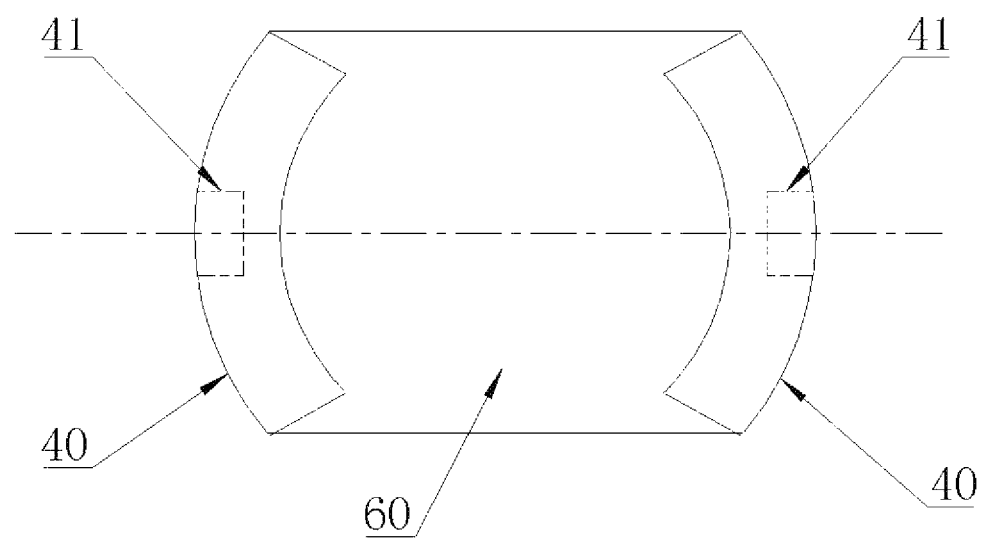
FIG. 10 is a top view of FIG. 9.

Referring to FIGS. 7 and 8 together, as one specific implementation mode of the unilateral nail holder provided in the application, the rear side of the lower end of the pushing core 31 is provided with a separating groove 34, the inner wall surface of the separating groove 34 is an arc-shaped curved surface of which the upper end and the lower end are respectively warped backward and the lower end forms a separating ramp.

In the embodiment, the rear side of the lower end of the pushing core 31 is provided with a recessed separating groove 34, the inner wall surface of the separating groove 34 is an arc-shaped curved surface, and the arc-shaped axis of the arc-shaped curved surface is arranged in the vertical direction. When the pedicle screw is clamped with the unilateral nail holder, the pushing core 31 is pulled upwards, and the lower end of the inner wall surface of the separating groove 34 slides upwards along the separating protrusion 32, such that the fixing hook 20 moves backward, the fixing hook 20 is withdrawn from the rear side of the clamping groove 11. Then the clamping groove 11 is aligned with the single side plate 40 of the pedicle screw, such that the single side plate 40 slides into the clamping groove 11 from bottom to top. Then the pushing core 31 is pushed downwards such that the pushing core 31 is reset. The lower end of the inner wall surface of the separating groove 34 slides downwards along the separating protrusion 32 until the separating protrusion 32 completely enters the separating groove 34. At this time, the fixing hook 20 is just inserted into the fixing hole 41 at the rear side of the single side plate 40 in the clamping groove 11, the single side plate 40 is limited in the clamping groove 11, and the clamping of the pedicle screw by the unilateral nail holder is realized.

Referring to FIGS. 7 and 8 together, as a specific implementation mode of the unilateral nail holder provided in the application, the separating protrusion 32 is received in the separating groove 34, and the front wall surface of the separating protrusion 32 is an arc-shaped curved surface of which the upper end and the lower end are respectively warped backward.

In the embodiment, the front wall surface of the separating protrusion 32 is an arc-shaped curved surface, and the arc-shaped axis of the arc-shaped curved surface is arranged in the vertical direction, such that the separating ramp does not jam when sliding along the separating protrusion 32. More specifically, the front wall surface of the separating protrusion 32 is matched with the inner wall surface of the separating groove 34, such that the separating protrusion 32 can enter the separating groove 34, the limiting of the pushing core 31 in the up and down direction is realized, and the pushing core 31 is prevented from sliding up and down when a unilateral nail holder is not used.

Referring to FIGS. 1-8 together, as a specific implementation mode of the unilateral nail holder provided in the application, a holding rod 10 includes a handle 13 and an extension rod 14.

The handle 13 is provided with a sliding hole 131 for receiving the upper end of the pushing core 31. The extension rod 14 is connected to the lower end of the handle 13, a clamping groove 11 is provided on the lower end surface of the extension rod 14, and a fixing hook 20 is elastically connected to the extension rod 14.

In this embodiment, the upper end of the extension rod 14 is fixedly installed on the lower end of the handle 13. The sliding hole 131 is arranged along the axis of the handle 13 such that the pushing core 31 slides in the sliding hole 131 in the axial direction of the handle 13. The clamping groove 11 is arranged at the lower end of the extension rod 14 and the opening is located at the lower end surface of the extension rod 14. The fixing hook 20 is elastically connected to the extension rod 14 such that the fixing hook 20 can enter the clamping groove 11 from the rear side in a free state. At that, the fixing hook 20 can be hooked into the fixing hole 41 at the rear side of the single side plate 40 in the clamping groove 11 under the action of elastic force when the unilateral nail holder is used. The sliding groove 12 may be arranged on the front side of the extension rod 14. More specifically, the rear side of the extension rod 14 is arranged with an elastic piece, the upper end of which is fixed to the rear side of the lower end of the extension rod 14, and the fixing hook 20 is fixed to the lower end of the elastic piece.

Referring to FIGS. 1, 4, 6, and 8 together, as a specific implementation mode of the unilateral nail holder provided in the application, the front side surface of the lower end of the pushing core 31 is recessed to form an operation space 311 for communicating with the installation groove 60 of the pedicle screw, and the upper end of the pushing core 31 is provided with a through hole 312 which communicates with the operation space 311 and which is for opposing to the installation groove 60.

In the embodiment, between two side plates 40 on the top of the pedicle screw is the installation groove 60 for installing a fixing screw. On a plane perpendicular to the long axis of the pushing core 31, the cross section of the front side surface of the pushing core 31 is arc-shaped, such that the front side surface of the lower end of the pushing core 31 is recessed to form an operation space 311, and the lower end of the pushing core 31 does not shield the installation groove 60. The axis of the through hole 312 coincides with the axial direction of the operation space 311, such that the through hole 312 of the upper end of the pushing core 31 is communicated with the operation space 311. Such that when the fixing screw is installed in the installation groove 60, a tool can pass through the through hole 312 and clamp the fixing screw to aligned with the installation groove 60, and installation of the fixing screw is facilitated. More specifically, the upper end of the pushing core 31, in a cylindrical shape, is provided as passing through the sliding hole 131 of the handle 13, and the through hole 312 is arranged along the axis of the upper end of the pushing core 31. The rear side of the upper end of the pushing core 31 extends downwards to form a lower end of the pushing core 31 having a semicircular cross section, and the through hole 312 extends downwards to form an operation space 311 at the front side of the lower end of the pushing core 31.

Figure 3:
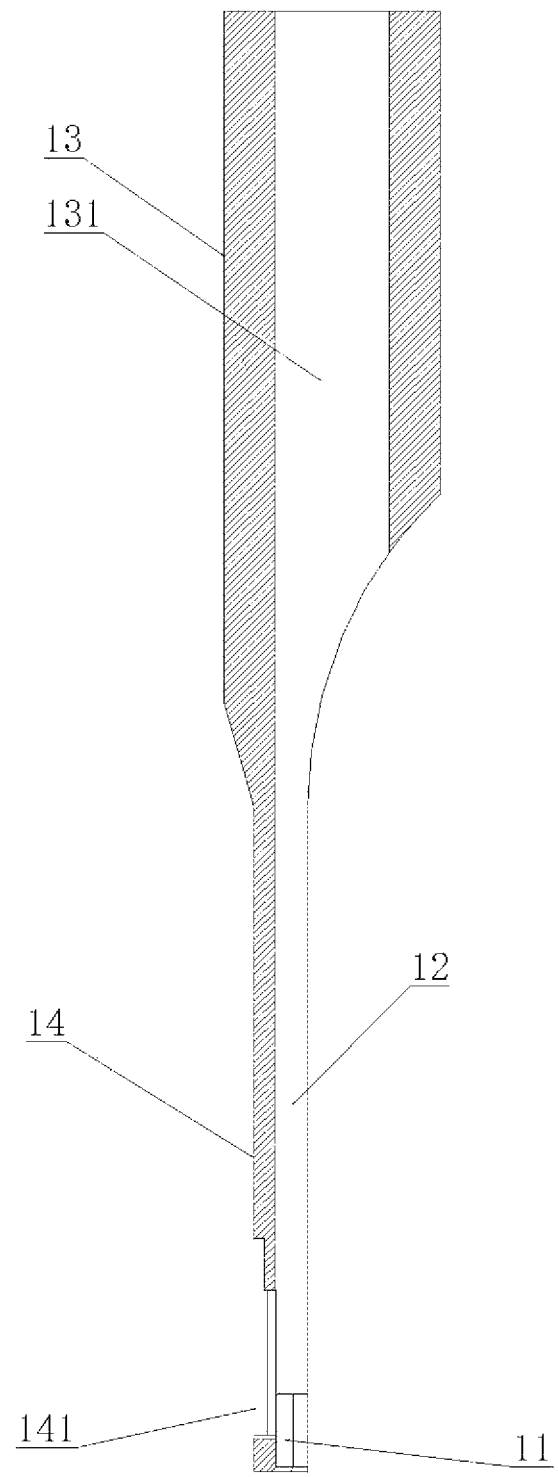
FIG. 3 is a sectional view at C-C in FIG. 2.
Figure 5:
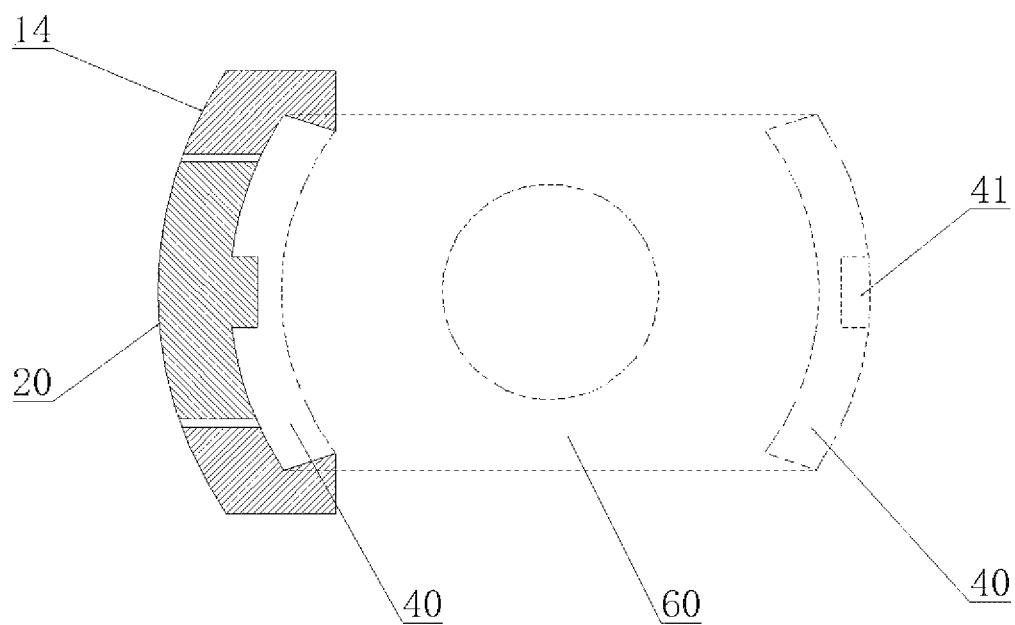
FIG. 5 is a sectional view at E-E in FIG. 4.
Figure 6:
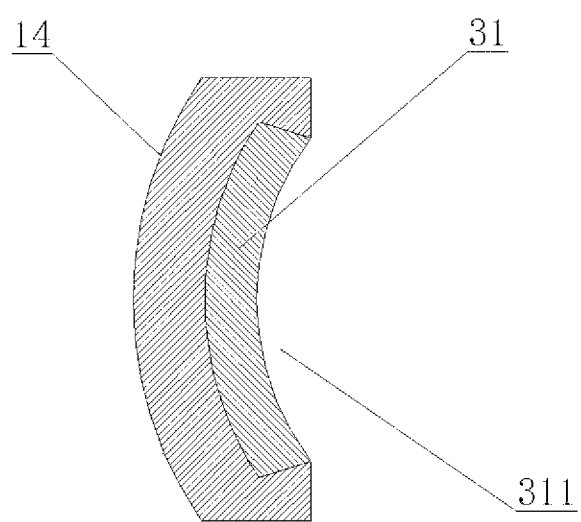
FIG. 6 is a cross-sectional view at F-F in FIG. 4.

Referring to FIGS. 3 to 5 as well as FIGS. 7 and 8 together, as a specific implementation mode of the unilateral nail holder provided in the application, the lower end of the extension rod 14 is provided with a receiving groove 141 communicating with the rear side of the clamping groove 11; the fixing hook 20 is provided in the receiving groove 141, and the hook portion of the fixing hook 20 penetrates into the clamping groove 11 from the receiving groove 141. The fixing hook 20 is prevented from protruding out of the surface of the extension rod 14.

In the embodiment, the receiving groove 141 is arranged at the rear side of the lower end of the extension rod 14, and at the rear side of the clamping groove 11, and opens rearwards. The groove bottom of the receiving groove 141 communicates with the rear side of the clamping groove 11 such that the hook portion of the fixing hook 20 can penetrate from the receiving groove 141 into the clamping groove 11.

Referring to FIG. 8 as well, as a specific implementation mode of the unilateral nail holder provided in the application, the lower side surface of the hook portion of the fixing hook 20 is a ramp inclined upward at the front end.

In the embodiment, the single side plate 40 of the pedicle screw is inserted into the clamping groove 11 from the bottom upward when the unilateral nail holder is used. The lower side surface of the hook portion of the fixing hook 20 is a ramp with the front end inclined upwards, such that the lower side surface of the hook portion of the fixing hook 20 can be pushed when the top of the single side plate 40 is inserted into the clamping groove 11 upwards, the fixing hook 20 moves backward, the hook portion of the fixing hook 20 is withdrawn from the clamping groove 11, and the single side plate 40 is smoothly inserted into the clamping groove 11. Then, the fixing hook 20 reenters the clamping groove 11 under the elastic force of the elastic piece and is hooked with the fixing hole 41 at the rear side of the single side plate 40.

Referring to FIGS. 4 and 5 together, as a specific implementation mode of the unilateral nail holder provided in the application, the front side of the clamping groove 11 is opened, and the width of the opening of the front side of the clamping groove 11 is smaller than the width of the rear side of the clamping groove 11. The front side of the clamping groove 11 is opened, such that the front side wall of the clamping groove 11 can be prevented from entering the installation groove 60 between the two side plates 40 of the pedicle screw, which influences the installation of the fixing screw. Since the width of the front side opening of the clamping groove 11 is smaller than the width of the rear side of the clamping groove 11, the single side plate 40 is not detached from the front side opening of the clamping groove 11.

Referring to FIG. 5 as well, as a specific implementation mode of the unilateral nail holder provided in the application, the clamping groove 11 has a fan-shaped cross section.

In this embodiment, the cross section of the lateral plate 40 of the pedicle screw is fan-shaped, and the cross section of the clamping groove 11 is fan-shaped to match the cross sectional shape of the lateral plate 40 of the pedicle screw, such that the lateral plate 40 of the pedicle screw can slide into the clamping groove 11 from the bottom upward without coming out of the front opening of the clamping groove 11.

The above are only preferred embodiments of the application and are not intended to limit the application. Any modification, equivalent replacement and improvement, and the like made within the spirit and principle of the application shall be included in the scope of the application.

Although embodiments of the present disclosure have been described in detail, it should be understood that various changes, substitutions and alterations can be made herein without departing from the spirit and scope of the disclosure as defined by the appended claims.

Moreover, the scope of the present disclosure is not intended to be limited to the particular embodiments described here. As one of ordinary skill in the art will readily appreciate from the disclosure of the present disclosure that processes, machines, manufacture, compositions of matter, means, methods, or steps, presently existing or later to be developed, may perform substantially the same function or achieve substantially the same result as the corresponding embodiments described herein. Accordingly, the appended claims are intended to include within their scope such processes, machines, manufacture, compositions of matter, means, methods, or steps.

The invention claimed is:
1. A unilateral nail holder, comprising:
   a holding rod, wherein a lower end of the holding rod is provided with a clamping groove for receiving a single side plate of a pedicle screw;
   a fixing hook connected to the holding rod, wherein the fixing hook is located at an inner rear side of the clamping groove, a rear side of the single side plate is provided with a fixing hole, and the fixing hook is used for hooking with the fixing hole; and a separating mechanism provided between the holding rod and the fixing hook for pushing the fixing hook out of the fixing hole; and wherein the separating mechanism comprises:

a pushing core slidably connected to the holding rod, and axially sliding along the holding rod;

a separating protrusion provided on the fixing hook; and a separating ramp provided at a lower end of the pushing core, wherein the separating ramp is in sliding fit with the separating protrusion, and is used for pushing the separating protrusion backward; and wherein a front side surface of the lower end of the pushing core is recessed to form an operation space for communicating with an installation groove of the pedicle screw.

2. The unilateral nail holder of claim 1, wherein a front side of the holding rod is provided with a sliding groove arranged along a long axis of the holding rod, and an inner wall of the sliding groove is provided with a limiting protrusion; and the pushing core is provided in the sliding groove in a sliding mode, and a side surface of the pushing core is provided with an abutting protrusion that is located above the limiting protrusion and is used for abutting against the limiting protrusion.

3. The unilateral nail holder of claim 2, wherein a lower end of the sliding groove is communicated with an upper end of the clamping groove, and the lower end of the pushing core is insertable into the clamping groove.

4. The unilateral nail holder of claim 1, wherein a rear side of the lower end of the pushing core is provided with a separating groove, an inner wall surface of the separating groove is an arc-shaped curved surface of which an upper end and a lower end are respectively warped backward, and the lower end forms the separating ramp; and the separating protrusion is received in the separating groove, and a front wall surface of the separating protrusion is an arc-shaped curved surface of which an upper end and a lower end are respectively warped backward.

5. The unilateral nail holder of claim 1, wherein the holding rod comprises:

a handle provided with a sliding hole for receiving an upper end of the pushing core; and an extension rod connected to a lower end of the handle, wherein the clamping groove is provided on a lower end surface of the extension rod, and the fixing hook is elastically connected to the extension rod.

6. The unilateral nail holder of claim 5, wherein the upper end of the pushing core is provided with a through hole communicated with the operation space and for being opposite to the installation groove.

7. The unilateral nail holder of claim 5, wherein a lower end of the extension rod is provided with a receiving groove communicating with the rear side of the clamping groove; and the fixing hook is provided in the receiving groove, and a hook portion of the fixing hook penetrates into the clamping groove from the receiving groove.

8. The unilateral nail holder of claim 1, wherein a front side of the clamping groove is opened, and a width of a front side opening of the clamping groove is smaller than a width of a rear side of the clamping groove.

* * * * *